(12) United States Patent
Hadas

(10) Patent No.: US 6,368,287 B1
(45) Date of Patent: Apr. 9, 2002

(54) INTEGRATED SLEEP APNEA SCREENING SYSTEM

(75) Inventor: Noam Hadas, Tel Aviv (IL)

(73) Assignee: S.L.P. Ltd., Tel Aviv (IR)

( * ) Notice: Subject to any disclaimer, the term of this patent is extended or adjusted under 35 U.S.C. 154(b) by 0 days.

(21) Appl. No.: 09/581,477
(22) PCT Filed: Jan. 5, 1999
(86) PCT No.: PCT/IL99/00008
§ 371 Date: Jun. 14, 2000
§ 102(e) Date: Jun. 14, 2000
(87) PCT Pub. No.: WO99/34864
PCT Pub. Date: Jul. 15, 1999

(30) Foreign Application Priority Data

Jan. 8, 1998 (IL) ................................................ 122875

(51) Int. Cl.⁷ ................................................ A61B 5/08
(52) U.S. Cl. ...................................... 600/529; 600/537
(58) Field of Search ................................ 600/529, 531, 600/532, 533, 537, 538; 128/204.23

(56) References Cited

U.S. PATENT DOCUMENTS

| | | | |
|---|---|---|---|
| 3,903,876 A | * 9/1975 | Harris | 600/537 |
| 4,648,407 A | * 3/1987 | Sackner | 600/534 |
| 4,715,367 A | * 12/1987 | Crossley | 600/27 |
| 4,777,962 A | * 10/1988 | Watson et al. | 600/529 |
| 4,802,485 A | * 2/1989 | Bowers et al. | 600/324 |
| 5,134,995 A | * 8/1992 | Gruenke et al. | 128/204.23 |
| 5,259,373 A | * 11/1993 | Gurenke et al. | 128/204.23 |
| 5,355,893 A | * 10/1994 | Mick et al. | 600/532 |
| 5,520,176 A | * 5/1996 | Cohen | 600/300 |
| 5,551,418 A | * 9/1996 | Estes et al. | 128/204.23 |
| 5,555,891 A | * 9/1996 | Eisenfeld | 600/534 |
| 6,142,950 A | * 11/2000 | Allen et al. | 600/529 |
| 6,165,133 A | * 12/2000 | Rapoport et al. | 600/529 |

* cited by examiner

Primary Examiner—Eric F. Winakur
Assistant Examiner—Navin Natnithithadha
(74) Attorney, Agent, or Firm—Mark M. Friedman

(57) ABSTRACT

This invention is a method, and device, suitable for use without professional medical supervision, for screening for sleep apnea. All elements of the device are housed in a small, flexible, plastic housing which is placed on the user's philtrum. A thermistor acquires data describing the respiratory pattern. A processor analyzes the respiratory pattern in real time and outputs a study result, describing the occurrence of any episodes of apnea, to a non-volatile colored marker on the plastic housing. A flashing LED display informs the user when placement of the device is appropriate. A lithium battery, which powers all elements of the device, is activated by a pull-tab removed by the user.

14 Claims, 3 Drawing Sheets

INTEGRATED SLEEP APNEA SCREENING SYSTEM

FIELD AND BACKGROUND OF THE INVENTION

The present invention relates to medical monitoring devices and, in particular, it relates to a monitor for the detection of sleep apnea.

It is known that sleep related breathing disorders are a common medical problem. Two common sleep pathology syndromes are Obstructive Sleep Apnea (OSA) and Central Sleep Apnea (CSA).

Obstructive Sleep Apnea (OSA) occurs when the upper airway (the nose, mouth or throat) become obstructed in some way during sleep, and is usually accompanied by a decrease in the oxygen saturation of the blood ($SpO_2$). Snoring indicates an intermittent obstruction, which at times may become complete, stopping air flow. Apnea (the cessation of breathing) may occur hundreds of times during one night of sleep, leading to severe sleep disruption and excessive daytime somnolence. As such, the patient may easily fall asleep during working hours, such as when the patient is driving a car or a truck. Many commercial trucking firms thus require that their drivers undergo sleep studies to determine if they suffer from OSA. Furthermore, OSA may cause heart problems such as cardiac arrhythmias and Cor Pulmonale.

Central Sleep Apnea Syndrome (CSA), in contrast, occurs due to a defect in central nervous system control of the respiratory drive, and is most commonly seen in patients with neurological disorders affecting respiratory control and in the elderly. CSA may also result in frequent awakenings and their associated impact on daytime performance.

Definitive diagnosis of these respiratory-sleep pathologies is currently achieved by means of an in-lab, full night, formal sleep study. In such a study, the patient is required to sleep for a whole night in a controlled environment (a "sleep laboratory") while connected to multiple monitoring devices, which continuously measure such physiological parameters as respiratory effort, nasal and oral airflow, brain electrical activity (EEG), muscle electrical activity (EMG), heart rate and rhythm (ECG), and blood oxygen saturation. These parameters are recorded on paper or stored in a memory bank for later analysis. A trained sleep technician is required to oversee the study so as to ensure that all parameters are recorded properly. The data is then analyzed, either manually or by specialized software, to produces a "hypnogram" which describes the nature of the patients sleep. Indices in the hypnogram, such as an "apnea index" and a "leg movement index", are then used, by a sleep specialist, to diagnose the patients pathology.

The formal sleep study as a means of diagnosing and following-up patients with respiratory related sleep problems, however, suffers from several deficiencies and limitations:

1. The study requires the use of multiple medical monitoring devices and the continuous presence of a trained technician. It is thus labor intensive to perform, and requires the use of multiple, expensive, resources.
2. The patient is asked to sleep in a non natural sleep environment, which may itself affect his sleep patterns.
3. The patient is inconvenienced by having to be in a hospital setting for a night.
4. There is no patient privacy.

As such, sleep laboratories are a limited resource, each containing only a limited number of beds. This is particularly problematic as studies are often conducted on "suspicious" patients in whom the outcome is frequently negative. In such patients, for whom there was no need for the study at all, a limited screening study may have been sufficient to exclude sleep pathology. The study price often prohibits repeating studies on a regular basis for purposes of patient follow-up.

In order to overcome some of these drawbacks, the performance of home studies by means of ambulatory systems has become popular. These studies utilize miniature ambulatory recorders, and are limited to a relatively small number of information recording channels. The patient is prepared for the study at the sleep lab, and returns home with all sensors appropriately attached. Alternatively, a technician may come to the patients home, or the patient may attach the sensors by himself after receiving appropriate instruction from a technician. The study is then conducted in the patient's home, as he sleeps in his own bed, and the recorded data stored in a memory device. In the morning the recorder and memory device are returned to the sleep lab for data downloading to an analysis station. Some of these ambulatory systems can correct for some data recording problems, by adjusting the gain or filtering during data recording or when post-processing the data. Alternatively, the study can be monitored from the sleep lab via a modem.

Although ambulatory sleep-apnea monitoring systems are much more convenient to the patient, and considerably less expensive than formal, in-lab, sleep studies, all current ambulatory sleep monitoring systems suffer from several deficiencies:

1. Performance of the study still requires the participation of a trained technician (for the purposes of either attaching the monitoring device or instructing the patient how to do so) and the participation of a formal sleep laboratory (for the purposes of downloading and analyzing the test results, and maintaining the equipment necessary for the performance of the test). Such tests are thus still labor and resource intensive.
2. As analysis of the recorded data is performed off-line in the sleep laboratory, the ambulatory monitoring device must be able to store all registered data in a suitable memory storage device, until such data can be downloaded. Alternatively, if the data is relayed to the sleep laboratory in real time, a modem and telephone line are necessary. Current ambulatory devices are therefore relatively complex and expensive to manufacture. As such, ambulatory studies are still too expensive to perform on a regular basis (currently approximately $500 per study), thus precluding their widespread use as a screening tool or for purposes of frequent patient follow-up. In addition, the cost of such studies does not justify their use on "difficult" patients, such as mental health patients or small children, in whom the likelihood of technical failure of the study is high.

There is therefore a need for a sleep-apnea screening system which is suitable for widespread use for patient screening and follow-up. Such a system should be sufficiently simple to implement as to allow patients to perform the study at home, without the need for assistance from a trained technician. In addition, such a system should provide the patient with an easily understandable result at the end of the study, without the need for data processing at a sleep laboratory, and without the need for interpretation of the result by a physician or technician. Finally, such a system should be sufficiently inexpensive as to make multiple and frequent studies practical to finance.

SUMMARY OF THE INVENTION

The present invention is an ambulatory sleep-apnea screening system. The invention integrates a minimal data collection and analysis system into a disposable, single use device that achieves data collection and analysis in real time, and outputs the study result in an easily understood format immediately following the study. The entire system is incorporated into a single small, flexible, plastic unit which can be easily positioned, or placed, under the patients nose, that is, upon the patients philtrum. The system is powered by a lithium battery, which is irreversibly activated by means of the patient pulling on a tab. Once activated, a respiration detector (such as that which measures temperature differences in an airflow, by which is meant a flow of inhaled and exhaled nasal or oral air) inputs data describing the pattern of respiration into a micro-processor, via an analog to digital converter. A flashing LED display indicates to the user that the device is correctly positioned. A software module detects the absence of hot airflow for a predetermined period—indicating apnea. Apnea duration is measured, normal breaths between apneas are counted, and, together with real-time clock information, the presence, and severity of, episodes of apnea is documented. Data can be sampled continuously, or in segments each a few minutes long, so as to conserve battery power. After a predefined period of time, non volatile output flags (in the form of heat sensitive colored dots) are set by the software. Once activated, the output flags undergo a permanent color change. As such, they produce an easily read hard copy of the study results, informing the user whether significant apnea was detected and whether a physician need be consulted. Hereinafter, output flags which undergo a permanent change in color when activated by heat are referred to as "heat sensitive permanent color display elements".

The integration, onto a respiratory sensor, of a sleep apnea screening system which is capable of analyzing respiratory data in real time and generating an immediate report thereof, is unique to the current invention. By "real time" is meant that the processing of the respiratory data and the sensing of the respiratory pattern occur during the same time interval, rather than the processing occurring after all respiratory sensing has been completed.

As data is analyzed in real time, the need for a large memory storage unit to store data for later analysis, and the need for complex downloading hardware, are obviated. This feature allows the entire system to be manufactured in a small and inexpensive format, and provides the user with the result of the study immediately upon conclusion of the study, without the need for data processing and analysis by medical professionals at a sleep laboratory. Furthermore, as the power source, processor, and display mechanism of the device are all integrated with the respiratory sensor into a small, single, unit, without the need for cables or wires connecting these components to each other, and as an easily seen flashing light confirms to the user that placement and operation of the device are correct, the device is simple and straightforward to use. The device can thus be operated without supervision by trained medical professionals. Accordingly, the cost per study is sufficiently low as to justify performing studies frequently for screening purposes (whenever there is even a slight chance of true pathology being present) or for regular patient follow-up. As their are no cables or wires connecting the respiratory sensor with the rest of the device, the possibility that the sensor might be pulled of off the users face, due to the cable becoming entangled while the user is asleep, is obviated.

It is an object of the current invention to provide a sleep apnea screening system which can be easily and reliably used by a patient without the need for professional supervision.

It is a further object of the current invention to provide a sleep apnea screening system which does not require the use of complex data storage and analysis hardware.

It is an additional object of the current invention to provide a sleep apnea screening system which is sufficiently simple and inexpensive as to facilitate performance of multiple sleep apnea screening studies on the same patient, on unreliable patents, or on patients with a low likelihood of having real pathology.

It is a vet further object of the current invention to provide a sleep apnea screening system which allows the study to be performed in the patients natural sleep environment.

It is a yet further object of the current invention to provide a sleep apnea screening system which does not infringe patient privacy.

According to the teachings of the present invention there is provided a sleep apnea screening system, including a respiration sensor, for sensing a respiratory pattern, at a location on a respiratory tract: a processor, for analyzing the respiratory pattern to determine the presence of a pattern of apnea, and for correlating the pattern of apnea with a diagnosis; a display, for displaying the diagnosis; a power source, for powering the respiration sensor, the processor, and the display; and a housing, for housing the processor, the display, and the power source, on the respiration sensor, the housing being placeable at the location on the respiratory tract. There is also provided a sleep apnea screening method, including the steps of placing a housing at a location on a respiratory tract; sensing a respiratory pattern at the housing during a time interval; processing the sensed respiratory pattern to detect the presence of a pattern of apnea, the processing occurring during the time interval; correlating the pattern of apnea with a diagnosis, the correlating occurring during the time interval; and displaying the diagnosis on the housing.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a sleep apnea screening system, integrated on an airflow sensor.

The principles and operation of a sleep apnea screening system, according to the present invention, may be better understood with reference to the drawings and the accompanying description.

Figure 1:
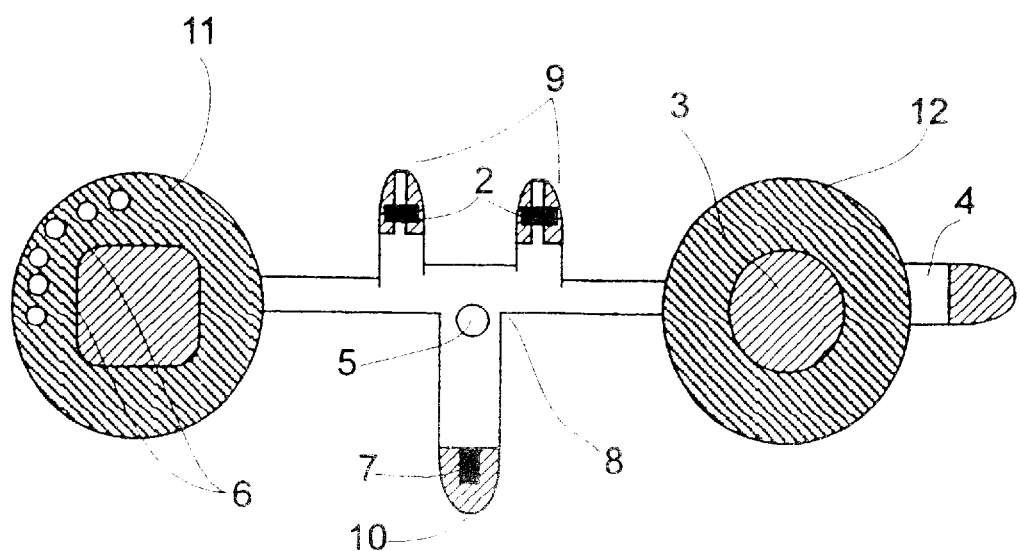
FIG. 1 is a line drawing of the physical structure of an apnea screening system.

Referring now to the drawings, FIG. 1 is a line drawing of the overall structure of the current invention. As can be seen, a thin, flexible housing 8, shaped like a thin strip, serves as a base for the system. In the preferred embodiment, housing 8 is made of a flexible plastic film. Housing 8 is shaped such that it can be attached between the nose and the upper lip of the user, such that protrusions 9 and 10 will overly the two nostrils and the mouth, respectively. Housing 8 includes two larger circles, 11 and 12, each approximately 1.5" in diameter, which house electronic components of the system. A double sided adhesive foam backing (not shown), covering the entire area of the back of housing 8, allows for the comfortable attachment of the device to the face of the user.

A power source 3, in the form of a flat lithium battery, is housed in circle 12. Power source 3 powers the functioning of all elements of the sleep apnea monitoring system. The negative contact of power source 3 is insulated from a conductive electrode (not shown) on housing 8 by a pull-tab 4. When tab 4 is pulled out by the user, contact is made between the negative contact of power source 3 and the electrode completing the electrical circuit, and operation of the system commences.

Two nasal NTC (Negative Temperature Coefficient) thermistors 2 and an oral NTC thermistor 7 are located on protrusions 9 and 10 respectively, such that they are located inside the air streams emanating from nose and mouth when housing 8 is properly positioned on the face of the user. Examples of thermistors suitable for use as nasal and oral thermistors 2 and 7 are SMT components (Thermometrics Inc., Tounton, UK). Alternatively, thermistors 2 and 7 can be replaced with other respiration sensors, such as humidity sensors, pressure sensors, or respiration sounds detectors. Thermistors 2 and 7 are connected in series to the input of a processor (CPU) 1, which is housed in circle 11. The flow of cyclically hot and cold air streaming over thermistors 2 and 7 (during expiration and inspiration respectively) causes a cyclical change in resistance within thermistors 2 and 7. This changing resistance is registered by CPU 1 as breathing data. In the preferred embodiment, CPU 1 is a RISC processor running a continuos monitoring and scoring program, which will be detailed below. CPU 1 analyzes the received respiratory data in real time, and reaches one of several possible predefined study conclusions.

A LED display 5 is located on housing 8 such that it can be easily seen by the user, when looking in a mirror, once the system has been attached to the face of the user and operation commenced. LED 5 is operative to flash with each breath taken by the user, so as to indicate that proper placement of thermistors 2 and 7 has been achieved ands that the system is functioning properly.

When the sleep apnea study is complete, CPU 1 issues a command to flow an electric current through one (or more) non-volatile markers 6. In the preferred embodiment, each one of markers 6 comprises a miniature heating element, and a coating of a heat sensitive material. When current is passed though one of the elements it heats up, inducing a change in the color of the coating material (such as rendering the coating material permanently black). This color change is permanent, even after cooling down of the element. Hereinafter, such markers are also referred to as "display elements". The choice of which of markers 6 to activate depends on the study conclusion, as determined by CPU 1. Each non-volatile marker 6 corresponds to one of several possible diagnoses. By "diagnoses" is meant possible study outcomes describing the degree of severity of apnea and recommended courses of action to be taken by the user in response thereto, for example:

1) Severe Apnea detected—must refer to a sleep lab
2) Medium Apnea detected—must refer to a sleep lab
3) Mild Apnea detected—Advised to consult your GP.
4) Possible problem—consult a physician,
5) No problem detected
6) Bad data—Perform a new study (if, for example, apneas lasting longer than 2 minutes were detected).

Figure 2:
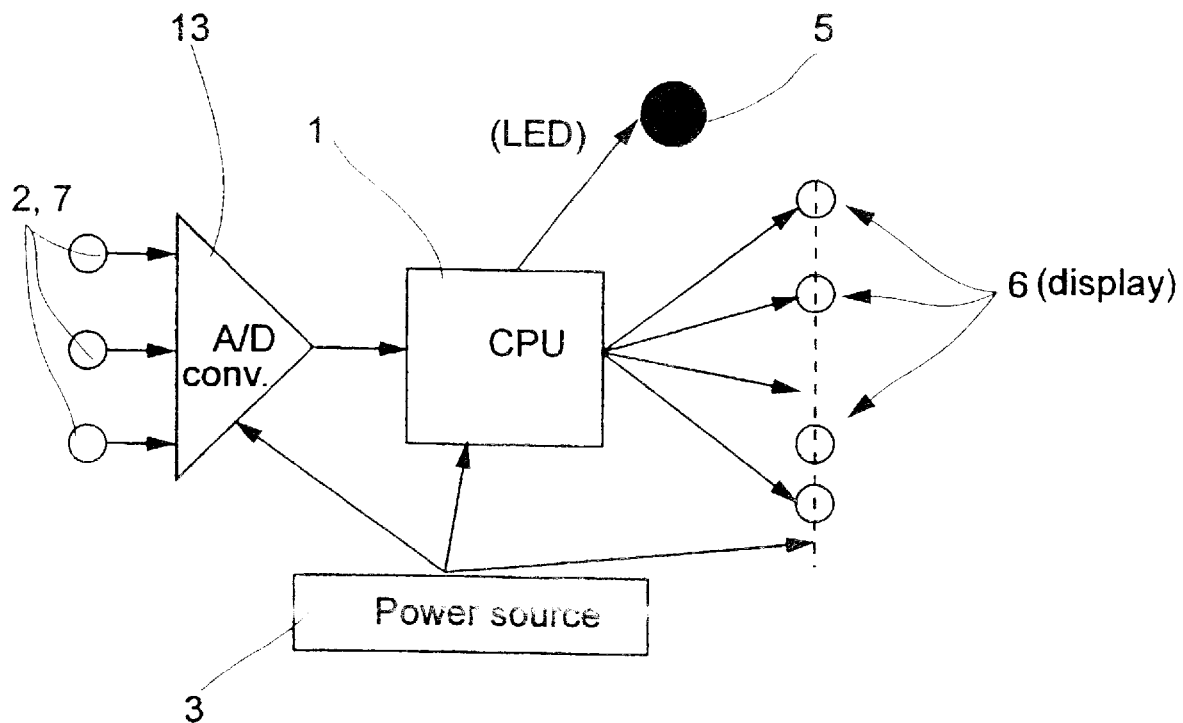
FIG. 2 is a schematic depiction of the structure of an apnea screening system.

In FIG. 2, a simplified block diagram of the device is shown. Thermistors 2 and 7 input flow data to a signal conditioner and A/D (analog to digital) converter 13, which may be part of CPU 1. The resultant digital data stream is input to CPU 1, which runs specialized data acquisition and analysis software. Each time a breath is sensed by thermistors 2 or 7, a command is output to LED 5, which flashes once. When a conclusion is reached at the end of the study, CPU 1 outputs a command to one of non-volatile markers 6. The entire system is powered by power source 3.

In normal operation, after switching the device on by pulling out tab 4, the user stands in front of a mirror, attaches the sensor under his nose and over his cheeks, and breathes through his nose and then through his mouth. If LED 5 flashes with each breath, the user knows that proper placement and operation of the device has been achieved. The user then waits approximately thirty minutes prior to going to sleep, during which time the device collects normal data, that is, respiratory data without episodes of apnea, over the course of several minutes. The user then goes to sleep. CPU 1 resumes collecting and processing data automatically after 1 hour, analyzes breathing patterns in real time for several minutes, and then enters a sleep mode for approximately 30 minutes. This cycle is then repeated several times, until CPU 1 reaches a conclusion as to whether sleep apnea was detected and estimates its severity, or until more than 5 hours have passed since the time that power source 3 was activated. CPU 1 then outputs the analysis result to non-volatile indicators 6. Upon awakening in the morning, the user checks to see which of indicators 6 have been activated, and is thus informed of the result of the study. In the event that significant apnea was detected during the study, the user is advised (by indicator 6) to consult with a physician or sleep clinic for further investigation. The device, with it's permanent color-coded study outcome, can be kept for later reference.

Figure 3:
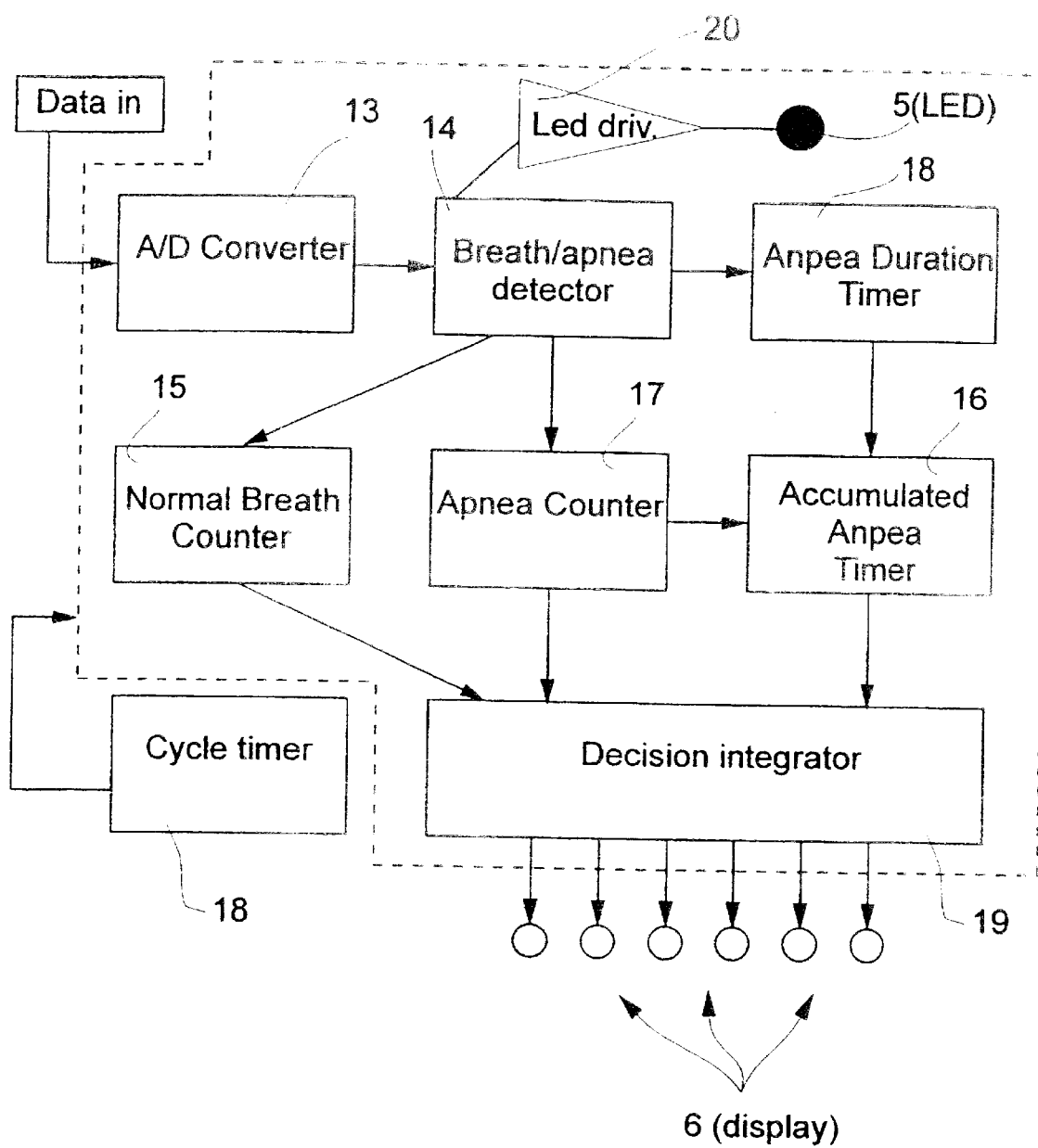
FIG. 3 is a block diagram of the data flow within the processor of an apnea screening system.

FIG. 3 describes the data flow within CPU 1 of the sleep apnea screening system.

Data in from thermistors 2 and 7 is smoothed and converted to digital format by A/D converter 13. The resultant digital data is input to a breath/apnea detector 14. Apnea detector 14 is a software module that monitors the data generated by thermistors 2 and 7, reflecting temperature differences caused by cold air being inhaled and hot air being exhaled. Apnea detector 14 locates the maximum and minimum registered temperatures, and calculates the difference between those values, which approximates the volume of inspired air. Apnea detector 14 also calculates the time from one maximum temperature value to the next. After processing several cycles during the thirty minute period prior to the user falling asleep (i.e. the period of no apnea), a maximum time between maximum temperature values is determined, and defined as the maximum normal time interval between breaths. In addition, a minimum percentage difference between maximum and minimum temperature values for one respiratory cycle is determined, and defined as the minimum normal peak-to-peak value of a breath. If the registered difference between the maximum and minimum temperatures of one cycle is less than the minimum normal peak-to-peak value, a low flow state can be defined as being present, while if the registered difference is zero, a zero flow state can be defined as being present. The condition of zero flow and undetectable rhythmic temperature pattern indicates the state of apnea, and this state is counted as a real apneac episode by an apnea counter 17 if it lasts for more than 10 seconds.

Apnea detector 14 thus locates local minima and maxima for each respiratory cycle, calculates the time from the last maxima to the current maxima, and calculates the peak to peak value of the current breath cycle. If the time from last breath is more than a prescribed value (typically 10 sec), or the peak-to-peak value is less than a prescribed value (typically 30%), an apnea mark is issued by apnea detector 14 and input to apnea counter 17. The number of normal breaths during the study period are counted by a normal breath counter module 15. The duration of each apneac episode is measured by an apnea duration timer 18. Apnea duration timer 18 commences timing once cessation of airflow is detected, and stops timing as soon as airflow resumes. This module also calculates the mean and standard deviation for all recorded apneac episodes during the study. The "accumulated apnea time", meaning the total number of minutes in apnea state during the course of the study, is calculated by an accumulated apnea timer 16. LED 5 is activated by apnea detector 14 via a LED driver 20 whenever a normal respiratory cycle is detected, and flashes.

The above described process is repeated several times, under the command of a cycle timer 18. Cycle timer 18 runs the data collection and analysis software in epochs of several minutes each every half hour, and then may switch CPU 1 to a sleep mode, in order to conserve battery power. Decision integrator 19 compares the data for each epoch with all prior epoch data, and when "convergence" of data (by which is meant approximately equivalent apnea behavior in several epochs) is detected, the data acquired during the study is assumed to be a reliable depiction of reality. When decision integrator 19 detects convergence of values, or when cycle timer 18 issues a command to decision integrator 19 after a predefined maximum period of time has elapsed (such as five hours), decision integrator 19 accesses all data stored in apnea counter 17, apnea duration timer 18, and accumulated apnea timer 16. Decision integrator 19 then compares the number and nature of apneac episodes detected to a predefined "diagnostic table" which categorizes all apnea patterns as falling into one of several diagnostic categories. Each diagnostic category corresponds to a particular non-volatile marker 6, which is activated by decision integrator 19 if the study is defined as falling into its corresponding diagnostic category. Based on the accumulated apnea time (as determined by accumulated apnea timer 16), the total number of apneac episodes per hour (as determined by apnea counter 17), and the breathing rate (as derived from the total breath count divided by the length of the study), decision integrator 19 activates one of the following markers 6:

"No problem" marker—no apnea detected.

"Minor problem" marker—average 1–5 apneas per hour.

"Moderate problem" marker—average 6–10 apneas per hour.

"Severe problem" marker—average over 10 apneas per hour.

"Bad study" marker—apneas lasting longer than 120 seconds detected, or a change of normal respiration amplitude over time of over 50% (poor steady state values), or a lack of normal respiration pattern during the first ten minutes after turn-on.

As the markers retain their appearance indefinitely, the device can be kept indefinitely as a medical record, and test results can be compared from study to study.

It will be appreciated that the invention as described herein may be supplemented in several ways, without departing from the spirit of the invention. For example, a heat sensitive element, to sense skin temperature during the study, may be incorporated into the device. This element would indicate if the device was removed during the night, prior to the end of the study. In addition, a light sensor may be incorporated into the device so as to determine that the lights were switched off during the study, as a fraud detection mechanism.

Figure 4:
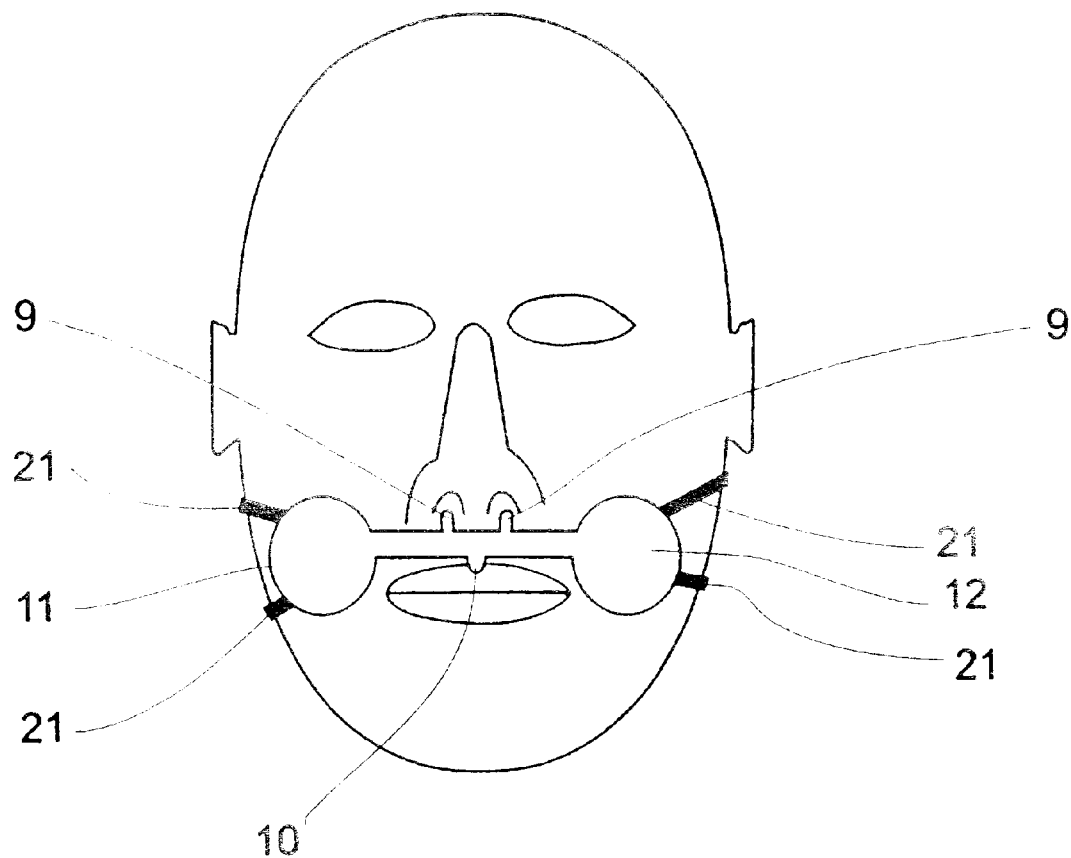
FIG. 4 is a diagram of the positioning of an apnea screening system on the face of a user.

FIG. 4 illustrates the preferred positioning of the device of the present invention on the face of the user. The device is positioned between the nose and the upper lip, covering the philtrum. In the preferred embodiment the device is held in place by double sided adhesive tape, although in alternative embodiments any mechanism suitable for securely holding an object against the face may be used, such as adjustable straps 21. As illustrated, protrusions 9 are positioned in proximity to the nares, protrusion 10 over the mouth, and circles 11 and 12 over the cheeks of the user.

As a very low cost screening method, the device of the current invention may have several applications:

1. Follow-up of sleep apnea patients after dietary treatment, surgery, CPAP treatment, fitting of an anti-snoring oral appliance, or a change is sleeping posture.
2. Screening infants for higher risk of Sudden Infant Death Syndrome (SIDS), by detecting non-regular breathing pattern.
3. Screening for candidates for a full feature sleep study.
4. Screening of applicants for high risk jobs like truck-driving or shift-working.

There has thus been described a sleep apnea screening system which can be easily and reliably used without the need for professional supervision or the use of complex data storage and analysis hardware. The system is sufficiently simple and inexpensive as to facilitate performance of multiple sleep apnea screening studies on the same patient, on unreliable patents, or on patients with a low likelihood of having real pathology. The system allows the study to be performed in the patients natural sleep environment, and does not infringe patient privacy.

What is claimed is:

1. A sleep apnea screening system, comprising
  a) a respiration sensor, for sensing a respiratory pattern, at a location on a respiratory tract;
  b) a processor, for analyzing said respiratory pattern to determine the presence of a pattern of apnea, and for correlating said pattern of apnea with a diagnosis;
  c) a display, for displaying said diagnosis;
  d) a power source, for powering said respiration sensor, said processor, and said display; and
  e) a housing, for housing said processor, said display, and said power source, on said respiration sensor, said housing being placeable at said location on said respiratory tract.

2. The system of claim 1, wherein said respiration sensor includes a thermistor.

3. The system of claim 1, wherein said location is a philtrum.

4. The system of claim 1, wherein said diagnosis is a degree of severity of apnea.

5. The system of claim 1, wherein said power source is a battery.

6. The system of claim 1, wherein said display is a heat sensitive permanent color display element.

7. The system of claim 1, wherein said housing is a flexible plastic unit.

8. The system of claim 1, wherein said processor comprises
   a) an analog to digital converter, for converting said sensed respiratory pattern into a digital signal;
   b) an apnea detector, for detecting episodes of apnea in said digital signal;
   c) an apnea duration timer, for timing the duration of said episodes of apnea;
   d) an apnea counter, for counting the number of said episodes of apnea;
   e) a normal breath counter, for counting the number of normal breaths in said digital signal;
   f) a decision integrator, for
      i) generating a description of a pattern of apnea from said number of episodes of apnea, said duration of episodes of apnea, and said number of normal breaths,
      ii) correlating said pattern of apnea with a diagnosis, and
      iii) informing said display to display said diagnosis; and
   g) a timer, for initiating and terminating operation of said analog to digital converter, said apnea detector, said apnea duration timer, said apnea counter, said normal breath counter, and said decision integrator.

9. A sleep apnea screening method, comprising the steps of
   a) placing a housing at a location on a respiratory tract;
   b) sensing a respiratory pattern at said housing during a time interval;
   c) processing said sensed respiratory pattern to detect the presence of a pattern of apnea, said processing occurring during said time interval,
   d) correlating said pattern of apnea with a diagnosis, said correlating occurring during said time interval; and
   e) displaying said diagnosis on said housing.

10. The method of claim 9, wherein said location is a philtrum.

11. The method of claim 9, wherein said sensing of said respiratory pattern is achieved by sensing a change in temperature of an airflow.

12. The method of claim 9, wherein said processing and said correlating are achieved by a processor located on said housing.

13. The method of claim 9, wherein said displaying is achieved by inducing a permanent color change in a display element on said housing.

14. The method of claim 9, wherein said housing is a flexible plastic unit.

* * * * *